US011517789B2

(12) United States Patent
Xie et al.

(10) Patent No.: US 11,517,789 B2
(45) Date of Patent: Dec. 6, 2022

(54) METHOD FOR MONITORING SWIMMING STATE BY MEANS OF WEARABLE DEVICE, AND WEARABLE DEVICE

(71) Applicant: GOERTEK INC., Weifang (CN)

(72) Inventors: Fuli Xie, Weifang (CN); Yifan Yang, Weifang (CN)

(73) Assignee: GOERTEK INC., Weifang (CN)

(*) Notice: Subject to any disclaimer, the term of this patent is extended or adjusted under 35 U.S.C. 154(b) by 959 days.

(21) Appl. No.: 16/327,597

(22) PCT Filed: Jul. 20, 2017

(86) PCT No.: PCT/CN2017/093724
§ 371 (c)(1),
(2) Date: Feb. 22, 2019

(87) PCT Pub. No.: WO2018/036316
PCT Pub. Date: Mar. 1, 2018

(65) Prior Publication Data
US 2019/0184233 A1 Jun. 20, 2019

(30) Foreign Application Priority Data
Aug. 25, 2016 (CN) .......... 201610725326.X

(51) Int. Cl.
A63B 24/00 (2006.01)
A61B 5/11 (2006.01)
(Continued)

(52) U.S. Cl.
CPC ........ A63B 24/0062 (2013.01); A61B 5/1121 (2013.01); A61B 5/1123 (2013.01);
(Continued)

(58) Field of Classification Search
CPC ........ A63B 24/0062; A63B 2024/0068; A63B 2220/40; A63B 2220/836; A63B 2244/20;
(Continued)

(56) References Cited

U.S. PATENT DOCUMENTS

2006/0161053 A1 7/2006 Heikkila
2014/0099615 A1* 4/2014 Sweeney .............. A61B 5/7405
434/254

(Continued)

FOREIGN PATENT DOCUMENTS

CN 10158442 A 9/2009
CN 101520815 A 9/2009
(Continued)

OTHER PUBLICATIONS

China First Office Action corresponding to Chinese Application No. 201610725326.X, dated Aug. 7, 2018.
(Continued)

Primary Examiner — Toan M Le
(74) Attorney, Agent, or Firm — Arent Fox Schiff LLP

(57) ABSTRACT

A method and a wearable device are provided. The method includes providing a swimming mode in the wearable device, and storing standard swimming stroke data that have been collected in advance as corresponding template data, when a monitoring process starts, activating the swimming mode according to an instruction given by a user who will immediately enter water, and after the swimming mode has been activated, controlling a sensor to collect swimming stroke data of the user; obtaining test data for identifying a swimming state of the user from the swimming stroke data; and matching the test data with each template data, when the test data successfully matches the template data, identifying the swimming state of the user to be the swimming state that corresponds to the template data.

12 Claims, 5 Drawing Sheets

(51) Int. Cl.
*A61B 5/00* (2006.01)
*A63B 71/06* (2006.01)

(52) U.S. Cl.
CPC ............ *A61B 5/7203* (2013.01); *A61B 5/725* (2013.01); *A61B 5/7246* (2013.01); *A63B 71/0619* (2013.01); *A61B 2503/10* (2013.01); *A63B 2024/0068* (2013.01); *A63B 2208/03* (2013.01); *A63B 2220/40* (2013.01); *A63B 2220/836* (2013.01); *A63B 2244/20* (2013.01)

(58) Field of Classification Search
CPC . A63B 2208/03; A61B 5/1121; A61B 5/1116; A61B 5/681; A61B 5/6824; A61B 5/7203; A61B 5/7246; A61B 5/725; A61B 5/72; A61B 2503/10
See application file for complete search history.

(56) References Cited

U.S. PATENT DOCUMENTS

| | | |
|---|---|---|
| 2015/0164377 A1 | 6/2015 | Nathan et al. |
| 2017/0357848 A1 | 12/2017 | Su |

FOREIGN PATENT DOCUMENTS

| | | |
|---|---|---|
| CN | 103908259 A | 7/2014 |
| CN | 104200234 A | 12/2014 |
| CN | 105159441 A | 12/2015 |
| CN | 105184325 A | 12/2015 |
| CN | 105786182 A | 7/2016 |
| CN | 105892674 A | 8/2016 |
| CN | 106175781 A | 12/2016 |
| GB | 2511833 A | 9/2014 |

OTHER PUBLICATIONS

China Search Report corresponding to Chinese Application No. 201610725326.X, dated Jul. 21, 2018.
International Search Report and Written Opinion corresponding to International Application No. PCT/CN2017/093724, dated Mar. 1, 2018.

* cited by examiner

METHOD FOR MONITORING SWIMMING STATE BY MEANS OF WEARABLE DEVICE, AND WEARABLE DEVICE

CROSS-REFERENCE TO RELATED APPLICATIONS

This application is a U.S. National Stage entry under 35 U.S.C. § 371 based on International Application No. PCT/CN2017/093724, filed on Jul. 20, 2017, which was published under PCT Article 21(2) and which claims priority to Chinese Patent Application No. 201610725326.X, filed on Aug. 25, 2016. The embodiment of the priority applications are hereby incorporated herein in their entirety by reference.

TECHNICAL FIELD

The present disclosure relates to the technical field of wearable devices, and particularly relates to a method for monitoring a swimming state by using a wearable device and a wearable device.

BACKGROUND

Sitting for long time at work results in obesity and various chronic diseases, which severely affect the life quality of people. For the sake of health, many people begin to participate in physical activities. Swimming, as a people's favorite aerobic exercise, can improve the cardiovascular system, the vital capacity, the capacity of the muscular system, and the thermoregulatory capacity. Swimming is also a sport that requires systemic participation, and can improve the strength and coordination of muscles, especially those of the trunk, shoulders and arms. Swimming need overcome a relatively large water resistance, so sticking to swimming can improve the strength, speed, endurance of muscles and the flexibility of joints.

Along with the growing interest in physical activities, smart sports watches have become a new favorite digital product. Movement state identification, as the technical basis of movement monitoring and movement state reminding, is the core of the algorithm of smart sports watches as well as one of the difficulties. There is not an effective technical solution of monitoring and identifying swimming movement states in the field of smart sports watches so far, which cannot satisfy the users' demand and result in poor experience of smart sports watches.

SUMMARY

The present disclosure provides a method for monitoring a swimming state by using a wearable device and a wearable device, to solve the problem in the prior art that there is not an effective technical solution of monitoring and identifying swimming movement states in the field of smart sports watches so far, which results in poor user experience of smart sports watches.

According to an aspect of the present disclosure, there is provided a method for monitoring a swimming state by using a wearable device, and the method comprises:

providing a swimming mode in the wearable device, and storing standard swimming stroke data that have been collected in advance as corresponding template data, when a monitoring process starts, activating the swimming mode according to an instruction given by a user who will immediately enter water, and after the swimming mode has been activated, controlling a sensor to collect swimming stroke data of the user;

obtaining test data from the swimming stroke data for identifying a swimming state of the user; and matching the test data with each template data, and when the test data that are successfully matched the template data exist, identifying the swimming state of the user to be the swimming state that corresponds to the template data associated with the test data that are successfully matched.

According to another aspect of the present disclosure, there is provided a wearable device, wherein the wearable device is provided therein with a sensor and a swimming mode, and the wearable device comprises:

a template storing unit, for storing standard swimming stroke data that have been collected in advance as corresponding template data, a test data collecting unit, for, when a monitoring process starts, activating the swimming mode according to an instruction given by a user who will enter water immediately, controlling the sensor to collect swimming stroke data of the user, and obtaining test data from the swimming stroke data for identifying a swimming state of the user, and a swimming state identifying unit, for matching the test data with each template data, and when the test data that are successfully matched the template data exist, identifying the swimming state of the user to be the swimming state that corresponds to the template data associated with the test data that are successfully matched.

The advantageous effects of the present disclosure areas follows. The method for monitoring a swimming state by using a wearable device according to the present disclosure comprises: providing a swimming mode in the wearable device, and storing standard swimming stroke data that have been collected in advance as corresponding template data, when a monitoring process starts, activating the swimming mode according to an instruction given by a user who will immediately enter water, and after the swimming mode has been activated, collecting the swimming stroke data of the user to obtain test data, matching the test data with each template data, to identify out the swimming state of the user. Compared with traditional sports watches, which can merely simply record information such as speed to estimate the information of the user such as calorie consumption, the present disclosure can accurately identify the swimming stroke used by the user in a swimming lap, which facilitates the user better knowing his own swimming movement state, and greatly helps improve the swimming stroke. In addition, according to the present disclosure, the user is merely required to switch the wearable device to the swimming mode before entering water and swimming, and the recording and analyzing of the swimming state data can be completed without any further operation in the swimming process, which simplifies the usage, and prevents the waterproof performance of the watch being harmed by underwater key pressing operations.

DETAILED DESCRIPTION

The design concept of the present disclosure is as follows. Regarding the problem in the prior art that conventional smart sports watches cannot monitor the swimming state when the user is swimming, the present disclosure proposes a solution of monitoring swimming movement state based on a wearable device. Specifically, accelerometer data of four standard swimming strokes are collected by using a Micro-Electro-Mechanical System (referred simply to as MEMS) sensor built in the wearable device and used as the preset template. After the user activates the swimming mode provided in the wearable device, the monitoring and identifying on the swimming state of the user can be realized in the swimming process without any operation by the user, thereby facilitating the user knowing the state of swimming this time, and improving the user experience.

First Embodiment

Figure 1:
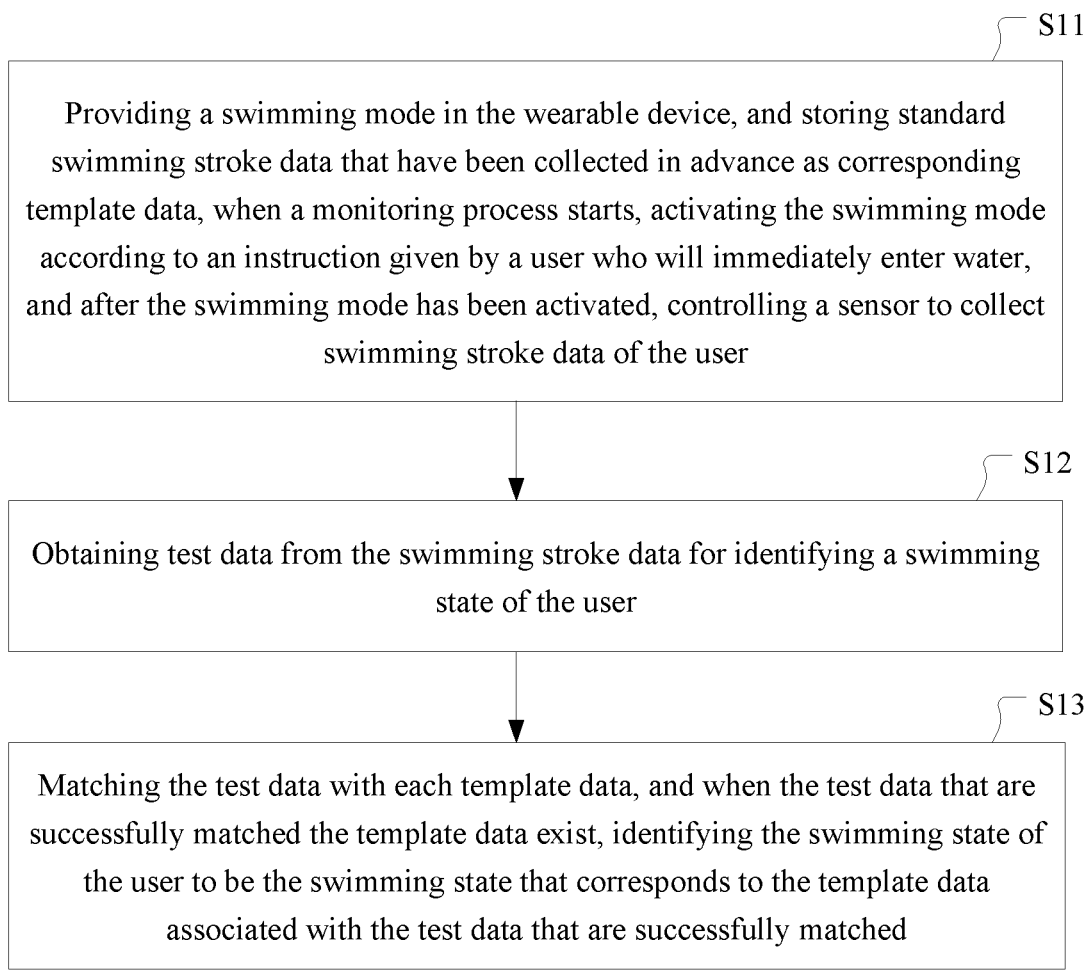
FIG. 1 is a flow chart of a method for monitoring a swimming state by using a wearable device according to an embodiment of the present disclosure.

FIG. 1 is a flow chart of a method for monitoring a swimming state by using a wearable device according to an embodiment of the present disclosure. Referring to FIG. 1, the method for monitoring a swimming state by using a wearable device of the present embodiment comprises:

Step S11, providing a swimming mode in the wearable device, and storing standard swimming stroke data that have been collected in advance as corresponding template data, when a monitoring process starts, activating the swimming mode according to an instruction given by a user who will immediately enter water, and after the swimming mode has been activated, controlling a sensor to collect swimming stroke data of the user. Here, the wearable device generally has a built-in three-axis acceleration sensor and can interact with the user via a screen. An example of the wearable device is a smart watch.

Step S12, obtaining test data from the swimming stroke data for identifying a swimming state of the user.

Step S13, matching the test data with each template data, and when the test data that are successfully matched the template data exist, identifying the swimming state of the user to be the swimming state that corresponds to the template data associated with the test data that are successfully matched.

It should be noted that, storing standard swimming stroke data that have been collected in advance as corresponding template data in Step S11 comprises: collecting standard swimming stroke data in advance, generating the template data according to the collected standard swimming stroke data and storing the template data in the wearable device. The standard swimming stroke data comprise at least breaststroke data, freestyle data, butterfly stroke data and backstroke data.

Identifying the swimming state of the user to be the swimming state that corresponds to the template data associated with the test data that are successfully matched in Step S13 comprises: identifying the swimming stroke of the user to be breaststroke, freestyle, butterfly stroke or backstroke that corresponds to the template data associated with the test data that are successfully matched.

It can be known from the method shown in FIG. 1 that, the method for monitoring a swimming state by using a wearable device according to the present embodiment can automatically identify the swimming state (such as swimming stroke) of the user, automatically identify the swimming stroke without any further operation after the user switches the smart watch to the swimming mode, and according to the identified-out swimming stroke, assist the user in acquiring more detailed movement information, for example, data of swimming this time, such as the rest time, swimming distance, stroke number and SWOLF, which facilitates the user more accurately knowing his own swimming movement state and improving the swimming efficiency. Where, the SWOLF index equals the sum of time taken in one lap and the number of strokes in one lap. The smaller the value of SWOLF is, the higher the efficiency of the swimming is.

Second Embodiment

Figure 2:
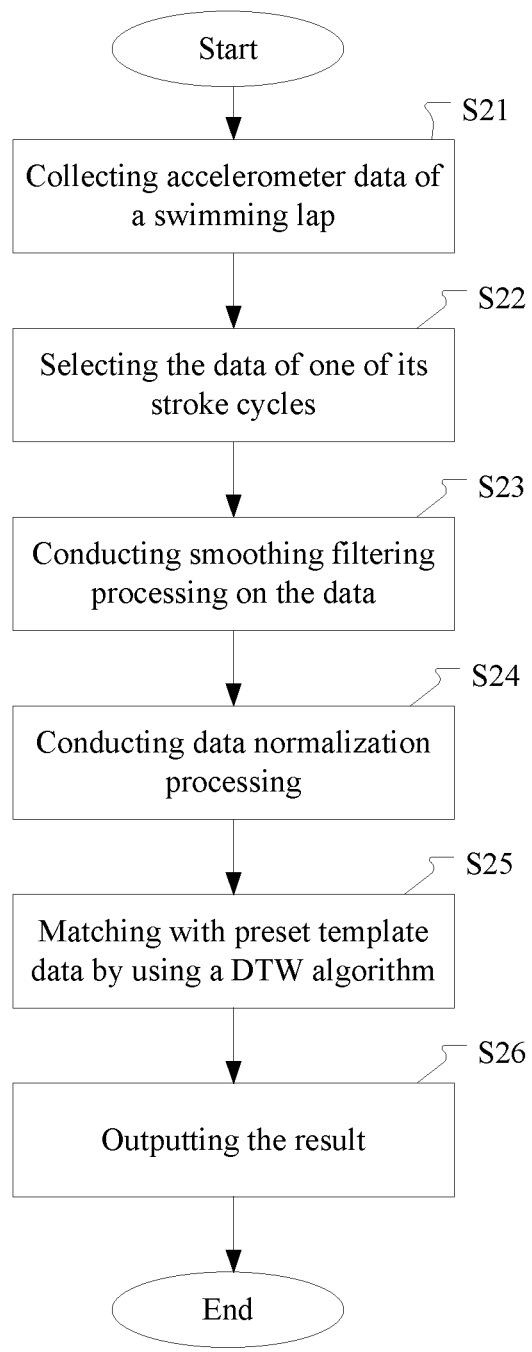
FIG. 2 is a flow chart of a method for monitoring a swimming state by using a wearable device according to another embodiment of the present disclosure.

FIG. 2 is a flow chart of a method for monitoring a swimming state by using a wearable device according to an embodiment of the present disclosure. Referring to FIG. 2, the method for monitoring a swimming state by using a wearable device of the present embodiment comprises:

The flow starts.

Step S21, accelerometer data of a swimming lap are collected.

In the present embodiment, first, the three-axis acceleration data of a swimming lap of the swimmer are collected by using an accelerometer (that is, acceleration sensor) in an MEMS sensor, to facilitate subsequently judging which swimming stroke the swimmer is using according to the matching result of the collected test data and the preset template data.

After the three-axis accelerometer data are collected when the user is swimming, the accelerometer data of a swimming lap may be saved in a buffer and be processed after the swimming lap finishes. It should be noted that, a swimming lap herein refers to a length of a swimming pool.

Step S22, data of one of the stroke cycles are selected.

On the basis of the acceleration data that were collected in Step S21, the data of one of the stroke cycles are selected. Usually, when swimming in a swimming pool, swimmers do not change the swimming stroke in a swimming lap. Therefore, it is merely required to collect the data of one stroke cycle in each swimming lap to realize identifying the swimming stroke in that swimming lap.

In the present embodiment, the selecting swimming stroke data of a stroke cycle from the swimming stroke data of a swimming lap of the user as the test data comprises: acquiring a total number of stroke cycles in the swimming lap of the user, and selecting the swimming stroke data of any stroke cycle other than the first stroke cycle and the last stroke cycle as the test data; or, acquiring a total number N of stroke cycles in the swimming lap of the user, and when N is an even number, selecting the swimming stroke data of the N/2 stroke cycle or the N/2+1 stroke cycle as the test data, and when N is an odd number, selecting the swimming stroke data of the (N+1)/2 stroke cycle as the test data.

It should be noted that, a stroke cycle refers to the time taken by the swimmer to complete a standard stroke action during swimming. Taking breaststroke as an example, a standard stroke action of breaststroke includes moving and kicking water outward, downward, backward, inward, and forward. The time taken by the swimmer to complete such a stroke action is a stroke cycle.

In the present embodiment, two methods are provided for selecting the acceleration data of one of the stroke cycles. In the first method, a total number of stroke cycles in a swimming lap of the user is acquired first. For example, by looking up the acceleration data of a swimming lap in the buffer, the total number of stroke cycles in the swimming lap is 12. Then, any stroke cycle other than the first stroke cycle and the last stroke cycle is selected as the test data to be identified. For example, the 5th stroke cycle is selected from the 2nd to the 11th stroke cycles as the test data. It should be noted that, the reason that the first stroke cycle and the last stroke cycle are excluded and are not selected for identifying is to improve the accuracy of identifying, because in each swimming lap, the action at the beginning and the action at the end have relatively large distortion, which is adverse to the identifying.

In the second method, a total number N of stroke cycles of the user in a swimming lap is acquired; when N is an even number, the swimming stroke data of the N/2 stroke cycle or the N/2+1 stroke cycle is selected as the test data, and when N is an odd number, the swimming stroke data of the (N+1)/2 stroke cycle is selected as the test data.

For example, if the total number N of stroke cycles is 12, the swimming stroke data of N/2 (that is, the 6th stroke cycle) or N/2+1 (the 7th stroke cycle) may be selected as the test data.

Figure 3:
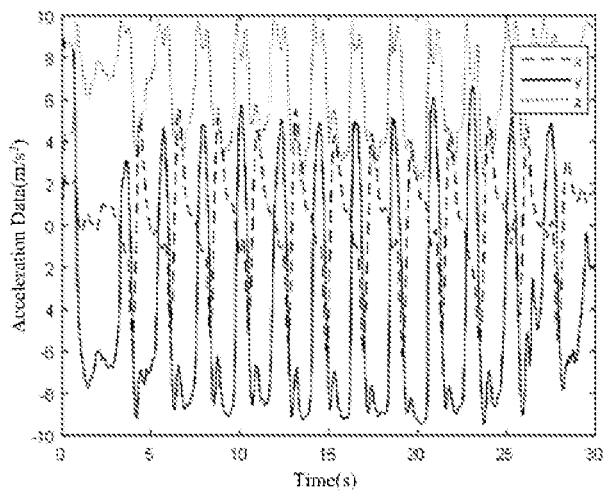
FIG. 3 is a waveform graph of three-axis accelerometer data of a breaststroke lap according to an embodiment of the present disclosure.
Figure 4:
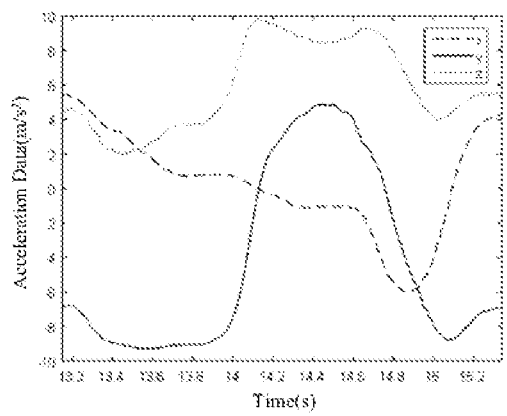
FIG. 4 is a waveform graph of accelerometer data selected from one of breaststroke stroke cycles according to an embodiment of the present disclosure.

FIG. 3 is the waveform graph of the three-axis accelerometer data of a breaststroke lap according to an embodiment of the present disclosure. FIG. 4 is the waveform graph of the selected accelerometer data of one of breaststroke stroke cycles according to an embodiment of the present disclosure. How to select the swimming stroke data of a stroke cycle is particularly described below by referring to FIGS. 3 and 4.

In the present embodiment, in axis direction data that correspond to a forward direction of swimming (for example, the data on the x-axis), selecting data between two neighboring waveform peak values which are used as end points as the swimming stroke data of a stroke cycle. In practical applications, on the collected acceleration data waveform graph, the acceleration data exhibit periodicity, but it is hard to determine when a period starts and ends. Therefore, just for the convenience of calculating, two neighboring waveform peak values on the acceleration data waveform graph are taken as the end points, and the data between the two end points are cut as a stroke cycle. Taking breaststroke as an example, FIG. 3 is a schematic waveform of saved accelerometer data of a breaststroke lap in a swimming pool of 25 meters, and the breaststroke lap includes totally 12 times of stroke. However, in each swimming lap, the action at the beginning and the action at the end have relatively large distortion, which is adverse to the identifying, and it can also be obviously seen from FIG. 3 that, the actions in the middle are relatively uniform. Therefore, a stroke cycle in the middle of the stroke cycles is selected as the selected data. FIG. 4 is a schematic waveform diagram of accelerometer data of a stroke cycle selected from the acceleration data shown in FIG. 3.

It should be noted that, in order to simplify the data calculation and improve the calculation efficiency, the present embodiment merely selects the data of a stroke cycle in the x-axis direction (the x-axis direction refers to the direction pointing to the fingers of the user when a smart sport watch is normally worn on the wrist of the user) in the three-axis acceleration data as the test data. It can be understood that, in other embodiments of the present disclosure, the y-axis or z-axis data may be selected, or all of the data of the three axes may be simultaneously selected as the test data, which is not limited.

Step S23, smoothing filtering processing is conducted on the data.

In the present embodiment, in order to avoid the influence of noise and improve the accuracy of swimming stroke identifying, the method further comprises: conducting smoothing filtering processing on the original waveform. Particularly, in the present embodiment, smoothing filtering processing is conducted on the selected swimming stroke data of a stroke cycle by using K time-nearest neighbor mean filtering, to filter out noise interference.

The K time-nearest neighbor mean filtering algorithm belongs to the prior art. In the K time neighbor equalization data processing, the time nearest neighbor numbers K is set in advance, and in the acceleration time sequences of each axis, the average value of a sequence consisting of K elements before a certain point and K elements after the certain point is taken as the value of the certain point after preprocessing. Regarding the first K data points and the last K data points of the time sequence, special processing should be conducted, and the neighboring data points used as the object of equalization processing should be as many as possible.

Step S24, data normalization processing is conducted.

In order to avoid the influence of the differences in the speeds, strengths and so on of different users and facilitate the data processing, in the present embodiment, data normalization processing is conducted on the filtered swimming stroke data, to normalize the filtered swimming stroke data into a range of ±10.

It is found by experimentation and statistical analysis that, the acceleration data in swimming are mainly within the range of plus and minus one time of the gravitational acceleration. Therefore, the present embodiment normalizes the filtered accelerometer data into the range of ±10.

Step S25, the data are matched with preset template data by using a DTW algorithm.

Regarding the processing of the three-axis accelerometer data, the commonly used method is combining the data of the three axes and then analyzing. The methods of combining mainly include: summation, first-order norm and second-order norm. When identifying the swimming stroke by using the accelerometer data, the variability of the accelerometer data of different swimming strokes should be as large as possible.

Figure 5:
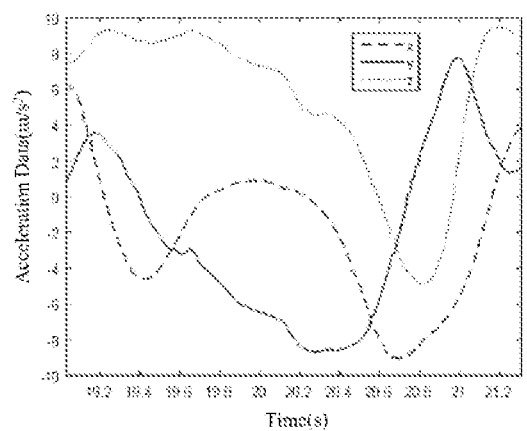
FIG. 5 is a waveform graph of accelerometer data selected from one of freestyle stroke cycles according to an embodiment of the present disclosure.
Figure 6:
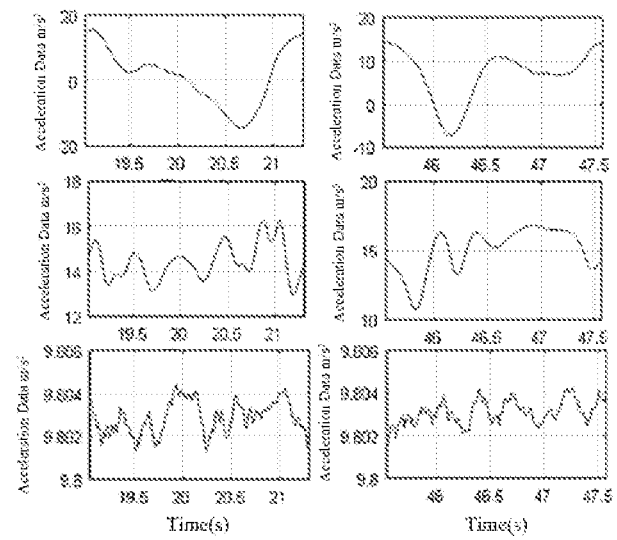
FIG. 6 is waveform graphs of summation, first-order norm and second-order norm of three-axis accelerometer data respectively corresponding to freestyle and breaststroke according to an embodiment of the present disclosure.

Freestyle and breaststroke may be taken as examples. FIG. 5 is a waveform graph of accelerometer data selected from one of freestyle stroke cycles according to an embodiment of the present disclosure. FIG. 6 is waveform graphs of summation, first-order norm and second-order norm of the three-axis accelerometer data respectively corresponding to freestyle and breaststroke according to an embodiment of the present disclosure. FIG. 6 is the comparison between the summation, first-order norm and second-order norm of the three-axis accelerometer of freestyle and breaststroke. In FIG. 6, the left column represents freestyle, and the right column represents breaststroke. The first line represents the summation of the axis accelerometer data, the second line represents the first-order norm of the axis accelerometer data, and the third line represents the second-order norm of the axis accelerometer data. It can be seen that, after the accelerometer data are solved to obtain the second-order norm, the numerical value variation range is merely approximately 0.02, which cannot be used for swimming stroke matching calculating and stroke cycle identifying. Similarly, first-order norm also has this problem, the numerical value variation range is relatively small, and the local peak values are too many. However, although the summation calculation saves a relatively complete acceleration value variation range, the variability of the two swimming strokes is not as rich as when the three-axis acceleration data are compared respectively.

Therefore, in the present embodiment, the three-axis acceleration values are calculated and compared, respectively. For a group of test data, data of each axis direction of three axis directions are matched respectively with data of corresponding axis direction in the template data, and a matching result of the group of test data is obtained according to the matching results of the three axis directions. That is, by using the DTW (Dynamic Time Warping) algorithm, a shortest DTW distance between the data of each axis direction of the group of test data that have been normalized and the data of the corresponding axis direction of each template data is calculated respectively, the shortest DTW distances of the axis directions are summated, and template data that have a minimum summation value are used as the template data associated with the group of test data. Particularly, the acquired three-axis data and the three-axis data that correspond to a certain swimming stroke in the template are analyzed respectively, the shortest DTW distances in the respective axis directions are calculated, and the shortest DTW distances of the three axis directions are summated. The smaller the summated value is, the higher the matching degree is. After the matching with four swimming stroke templates is completed, the swimming stroke having the highest matching degree with the template will be the swimming stroke used by the user.

Figure 7:
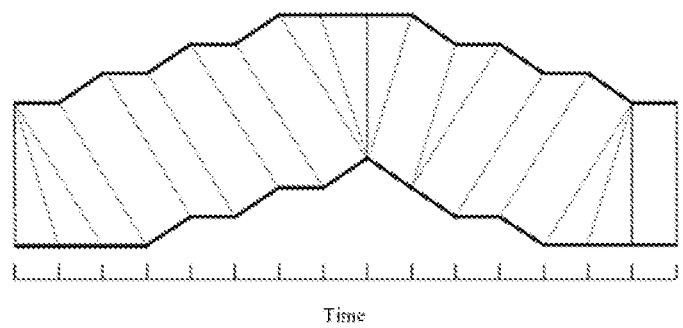
FIG. 7 is a schematic diagram of the warp of two time sequences according to an embodiment of the present disclosure.

In particular implementing, matching calculation is conducted on the data that have been normalized and the preset swimming stroke template data by using DTW algorithm. The algorithm is based on the concept of Dynamic Programming (DP), and calculates the similarity between two time sequences by extending and shortening the time sequences, which effectively solves the problem of template matching when the data durations are not the same. As shown in FIG. 7, the two solid lines at the top and the bottom are two time sequences, and the dotted line therebetween represents the similar points of the two time sequences. DTW uses the sum of the distances between all of those similar points, which is referred to as a warp path distance. The warp path distance is used to measure the similarity between two time sequences.

The particular process of the DTW algorithm is as follows:

It is assumed that the two time sequences whose degree of similarity is to be calculated are X and Y, and their lengths are |X| and |Y| respectively. The form of the Warp Path is $W=w_1, w_2, \ldots w_k$, where $\max(|X|, |Y|) \leq K \leq |X|+|Y|$. The form of $w_k$ is (i, j), where i represents the i coordinate in X, and j represents the j coordinate in Y. The warp path W must start with $w_1=(1, 1)$, and end with $w_k=(|X|, |Y|)$, to ensure that all of the coordinates in X and Y exist in W. In addition, i and j must be monotonically increased, to ensure that the dotted lines in FIG. 7 do not intersect, and the Warp Path finally obtained is the Warp Path having the shortest distance $$D(i,j)=\mathrm{Dist}(i,j)+\min[D(i-1,j),D(i,j-1),D(i-1,j-1)].$$

Figure 8:
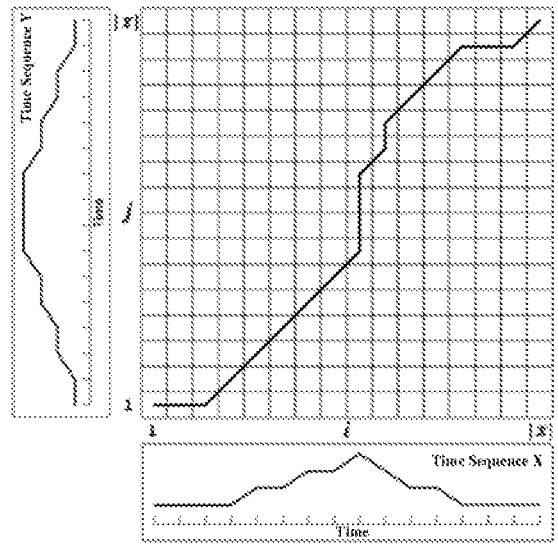
FIG. 8 is a schematic diagram of a cost matrix in the DTW algorithm according to an embodiment of the present disclosure.
Figure 9:
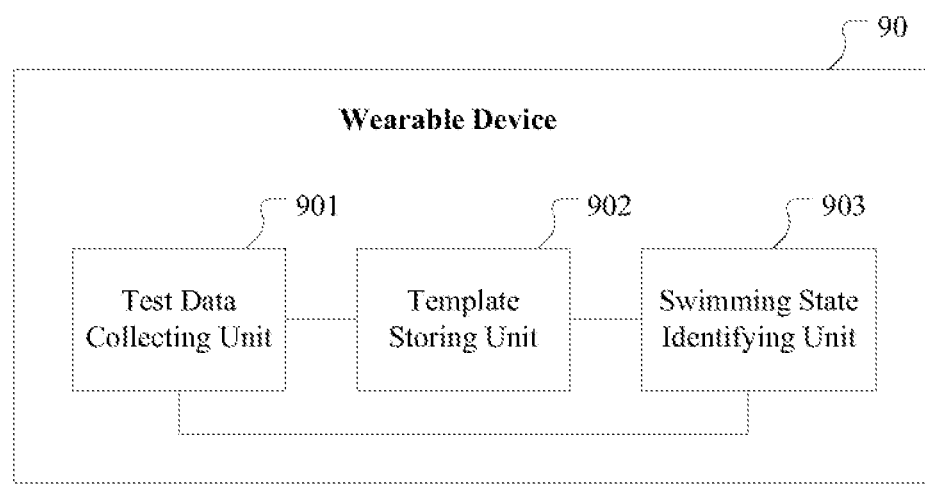
FIG. 9 is a structural block diagram of a wearable device according to an embodiment of the present disclosure.

FIG. 8 shows the warp path having the shortest distance between the cost matrix D and two time sequences in a DTW algorithm. In FIG. 8 the solid line represents the warp path. By using the DTW algorithm, matching calculation is conducted to the accelerometer data waveform of a stroke cycle that has been normalized and a preset template, and the swimming stroke that corresponds to the obtained shortest path value is determined as the swimming stroke used by the user.

It should be noted that, the DTW algorithm belongs to the prior art, and the details of the algorithm that are not described in the present embodiment may refer to the description in the prior art, which are not repeated here.

Step S26, the result is outputted.

After calculating the swimming stroke used by the user in swimming according to the DTW algorithm, the basic data that reflect the swimming sport efficiency may further be calculated and obtained, such as the time taken in a lap, the time taken in a stroke cycle, the stroke number in a lap and the swimming stroke. All other movement data including the SWOLF value, the stroke speed and so on can be obtained by converting by using the four types of data. The result obtained by the identifying and calculating is outputted to the user, thereby facilitating the user knowing his own swimming state, and assisting the user in adjusting the swimming stroke, which improves the user experience in using the smart watch.

By now, the flow ends.

Accordingly, the accelerometer data of four standard swimming strokes are collected by using the accelerometer in the smart watch as the preset template; after the user activates the swimming mode provided in the wearable device, when each swimming lap ends, the accelerometer data of one of its stroke cycles are selected as the test data, and matched with the prestored swimming stroke template parameters by using the DTW dynamic time warping algorithm, thereby identifying and obtaining the swimming stroke used by the user in the swimming lap. In the swimming process, the monitoring and identifying of the swimming state of the user can be realized without any further operation by the user, which optimizes the user experience, and improves the competitiveness of the smart watch.

Third Embodiment

In another embodiment of the present disclosure, there is further provided a wearable device 90. The wearable device 90 is provided with a sensor, a processor and a memory. Furthermore, according to the actual function of the wearable device, the wearable device may also comprise other hardware, which is not discussed here further.

The memory stores machine executable instruction codes, for example, instruction codes for instructing the swimming mode.

The processor communicates with the memory, reads and executes the machine executable instruction codes stored in the memory, to implement the steps of the method for monitoring a swimming state by using a wearable device disclosed in the first embodiment or the second embodiment of the present application.

Here, the memory may be any electronic, magnetic, optical or other physical storage devices, and may contain or store information, such as executable instructions, data. For example, the machine readable storage medium may be a RAM (Radom Access Memory), a volatile memory, a non-volatile memory, a flash memory, a storage driver (such as a hard disk drive), a solid state disk, any type of memory discs (such as an optical disk, DVD), or like storage media, or a combination thereof.

In terms of functions, the wearable device 90 comprises:

a template storing unit 902, for storing standard swimming stroke data that have been collected in advance as corresponding template data;

a test data collecting unit 901, for, when a monitoring process starts, activating the swimming mode according to an instruction given by a user who will immediately enter water, controlling the sensor to collect swimming stroke data of the user, and obtaining test data for identifying a swimming state of the user from the swimming stroke data; and a swimming state identifying unit 903, for matching the test data with each template data, and when the test data that are successfully matched the template data exist, identifying the swimming state of the user to be the swimming state that corresponds to the template data associated with the test data that are successfully matched.

In an embodiment of the present disclosure, the template storing unit 902 is particularly for collecting standard swimming stroke data in advance, generating the template data according to the collected standard swimming stroke data and storing the template data in the wearable device. The standard swimming stroke data comprise at least breaststroke data, freestyle data, butterfly stroke data and backstroke data.

The swimming state identifying unit 903 is for identifying the swimming stroke of the user to be breaststroke, freestyle, butterfly stroke or backstroke that corresponds to the template data associated with the test data that are successfully matched.

The sensor is a three-axis acceleration sensor, and the test data collecting unit 901 is particularly for controlling the three-axis acceleration sensor to collect three-axis acceleration data of the swimming stroke of the user, to obtain the test data.

The swimming state identifying unit 903 is particularly for, for a group of test data, matching data of each axis direction of the three axis directions respectively with data of corresponding axis direction in the template data, and obtaining a matching result of the group of test data according to the matching results of the three axis directions.

In an embodiment of the present disclosure, the test data collecting unit 901 is particularly for selecting swimming stroke data of a stroke cycle from the swimming stroke data of a swimming lap of the user as the test data.

The test data collecting unit 901 is for acquiring a total number of stroke cycles in the swimming lap of the user, and selecting the swimming stroke data of any stroke cycle other than the first stroke cycle and the last stroke cycle as the test data; or, acquiring a total number N of stroke cycles in the swimming lap of the user, and when N is an even number, selecting the swimming stroke data of the N/2 stroke cycle or the N/2+1 stroke cycle as the test data, and when N is an odd number, selecting the swimming stroke data of the (N+1)/2 stroke cycle as the test data.

In an embodiment of the present disclosure, the test data collecting unit 901 is for, in axis direction data that correspond to a forward direction of swimming, selecting data between two neighboring waveform peak values which are used as end points as the swimming stroke data of a stroke cycle.

In an embodiment of the present disclosure, the wearable device 90 further comprises: a data processing unit, for conducting smoothing filtering processing on the select swimming stroke data of a stroke cycle by using K time-nearest neighbor mean filtering, to filter out noise interference; and conducting data normalization processing on the filtered swimming stroke data, to normalize the filtered swimming stroke data into a range of ±10.

In an embodiment of the present disclosure, the swimming state identifying unit 903 is particularly for, by using dynamic time warping DTW, calculating the shortest DTW distance between the data of each axis direction of the group of test data that have been normalized and the data of the corresponding axis direction of each template data respectively, summating the shortest DTW distances of the axis directions, and using template data that have a minimum summation value as the template data associated with the group of test data.

It should be noted that, the wearable device of the present embodiment may be used in the above method for monitoring a swimming state by using a wearable device, and therefore the content of the working process of the wearable device that is not described in the present embodiment may be seen in the particular description of the above embodiment, which is not discussed here further.

In conclusion, the method for monitoring a swimming state by using a wearable device according to the present disclosure comprises: providing a swimming mode in the wearable device, and storing standard swimming stroke data that have been collected in advance in advance as corresponding template data; when a monitoring process starts, activating the swimming mode according to an instruction given by a user who will immediately enter water, and after the swimming mode has been activated, collecting the swimming stroke data of the user to obtain test data; and matching the test data with each template data, to identify out the swimming state of the user. Compared with traditional sports watches, which can merely simply record information such as speed to estimate the information of the user such as calorie consumption, the present disclosure can more accurately identify the swimming stroke used by the user in a swimming lap, which facilitates the user better knowing his own swimming movement state, and greatly helps improve the swimming stroke. In addition, according to the present disclosure, the user is merely required to switch the smart watch to the swimming mode before entering water and swimming, and the recording and analyzing of the swimming state data can be completed without any further operation in the swimming process, which simplifies the usage, and prevents the waterproof performance of the watch being harmed by underwater key pressing operations.

The above is merely preferable embodiments of the present disclosure, and is not intended to limit the protection scope of the present disclosure. Any modifications, equivalent substitutions or improvements that are made within the spirit and principle of the present disclosure shall all be included in the protection scope of the present disclosure.

What is claimed is:

1. A method for monitoring a swimming state by using a wearable device, comprising:

providing a swimming mode in the wearable device, and storing standard swimming stroke data that has been collected in advance as corresponding template data, when a monitoring process starts, activating the swimming mode according to an instruction given by a user who will immediately enter water, and after the swimming mode has been activated, controlling a sensor to collect swimming stroke data of the user;

obtaining test data from the swimming stroke data for identifying a swimming state of the user; and matching the test data with each template data, and when the test data that is successfully matched to the template data exist, identifying the swimming state of the user to be the swimming state that corresponds to the template data associated with the test data that is successfully matched, wherein the controlling of the sensor to collect swimming stroke data comprises controlling the sensor to collect three-axis acceleration data of the swimming stroke of the user by using a three-axis acceleration sensor, and obtaining the test data, wherein the matching of the test data with each template data comprises, for a group of test data, matching data of each axis direction of the three axis directions respectively with data of corresponding axis direction in the template data, and obtaining a matching result of the group of test data according to matching results of the three axis directions, and wherein the matching data of each axis direction of the three axis directions respectively with data of corresponding axis direction in the template data, and obtaining the matching result of the group of test data according to the matching results of the three axis directions comprises, by using dynamic time warping DTW, calculating a shortest DTW distance between the data of each axis direction of the group of test data that have been normalized and the data of the corresponding axis direction of each template data respectively, summating shortest DTW distances of the axis directions, and using template data that have a minimum summation value as the template data associated with the group of test data.

2. The method according to claim 1, wherein the step of storing standard swimming stroke data that have been collected in advance as corresponding template data comprises:

collecting standard swimming stroke data in advance, generating the template data according to the collected standard swimming stroke data and storing the template data in the wearable device, wherein the standard swimming stroke data comprise at least breaststroke data, freestyle data, butterfly stroke data and backstroke data; and the step of identifying the swimming state of the user to be the swimming state that corresponds to the template data associated with the test data that are successfully matched comprises:

identifying the swimming stroke of the user to be breaststroke, freestyle, butterfly stroke or backstroke that corresponds to the template data associated with the test data that are successfully matched.

3. The method according to claim 1, wherein the step of controlling a sensor to collect swimming stroke data of the user comprises:

controlling the sensor to collect and obtain swimming stroke data of a swimming lap of the user; and selecting swimming stroke data of a stroke cycle from the swimming stroke data of the swimming lap of the user as the test data.

4. The method according to claim 3, wherein the step of selecting swimming stroke data of a stroke cycle from the swimming stroke data of the swimming lap of the user as the test data comprises:

acquiring a total number of stroke cycles in the swimming lap of the user, and selecting the swimming stroke data of any stroke cycle other than a first stroke cycle and a last stroke cycle as the test data; or acquiring a total number N of stroke cycles in the swimming lap of the user, and when N is an even number, selecting the swimming stroke data of the N/2 stroke cycle or the N/2+1 stroke cycle as the test data, and when N is an odd number, selecting the swimming stroke data of the (N+1)/2 stroke cycle as the test data.

5. The method according to claim 3, wherein the step of selecting swimming stroke data of a stroke cycle from the swimming stroke data of the swimming lap of the user as the test data comprises:

in axis direction data that correspond to a forward direction of swimming, selecting data between two neighboring waveform peak values which are used as end points as the swimming stroke data of a stroke cycle.

6. The method according to claim 3, further comprising:

conducting smoothing filtering processing on the selected swimming stroke data of a stroke cycle by using K time-nearest neighbor mean filtering, to filter out noise interference; and conducting data normalization processing on the filtered swimming stroke data, to normalize the filtered swimming stroke data into a range of ±10.

7. A wearable device comprising:

a three-axis acceleration sensor;

a memory; and a processor configured to:

store, in the memory, standard swimming stroke data that has been collected in advance as corresponding template data;

when a monitoring process starts, activate the swimming mode according to an instruction given by a user who will immediately enter water, control the sensor to collect swimming stroke data of the user, obtain test data from the swimming stroke data for identifying a swimming state of the user, control the three-axis acceleration sensor to collect three-axis acceleration data of the swimming stroke of the user, and obtain the test data;

match the test data with each template data, and when the test data that is successfully matched to the template data exist, identify the swimming state of the user to be the swimming state that corresponds to the template data associated with the test data that is successfully matched;

for a group of test data, match data of each axis direction of the three axis directions respectively with data of corresponding axis direction in the template data; and obtain a matching result of the group of test data according to the matching results of the three axis directions, by using dynamic time warping DTW, calculating a shortest DTW distance between the data of each axis direction of the group of test data that has been normalized and the data of the corresponding axis direction of each template data respectively, summating shortest DTW distances of the axis directions, and using template data that has a minimum summation value as the template data associated with the group of test data.

8. The wearable device according to claim 7, wherein the processor is further configured to:
collect standard swimming stroke data in advance, generating the template data according to the collected standard swimming stroke data and storing the template data in the wearable device, wherein the standard swimming stroke data comprise at least breaststroke data, freestyle data, butterfly stroke data and backstroke data; and
identify the swimming stroke of the user to be breaststroke, freestyle, butterfly stroke or backstroke that corresponds to the template data associated with the test data that are successfully matched.

9. The wearable device according to claim 7, wherein the processor is further configured to control the sensor to collect swimming stroke data of a swimming lap of the user; and selecting swimming stroke data of a stroke cycle from the swimming stroke data of the swimming lap of the user as the test data.

10. The wearable device according to claim 9, wherein the processor is further configured to acquire a total number of stroke cycles in the swimming lap of the user, and select the swimming stroke data of any stroke cycle other than a first stroke cycle and a last stroke cycle as the test data; or
acquire a total number N of stroke cycles in the swimming lap of the user, and when N is an even number, select the swimming stroke data of the N/2 stroke cycle or the N/2+1 stroke cycle as the test data, and when N is an odd number, select the swimming stroke data of the (N+1)/2 stroke cycle as the test data.

11. The wearable device according to claim 9, wherein the processor is further configured, in axis direction data that correspond to a forward direction of swimming, to select data between two neighboring waveform peak values which are used as end points as the swimming stroke data of a stroke cycle.

12. The wearable device according to claim 9, wherein the processor is further configured to conduct a smoothing filtering processing on the selected swimming stroke data of a stroke cycle by using K time-nearest neighbor mean filtering, to filter out noise interference; and conduct data normalization processing on the filtered swimming stroke data, to normalize the filtered swimming stroke data into a range of ±10.

* * * * *